US006878519B1

(12) United States Patent
Parker et al.

(10) Patent No.: US 6,878,519 B1
(45) Date of Patent: Apr. 12, 2005

(54) DNA PROBES FOR SPECIFIC GENES OF ANTHRAX

(75) Inventors: Jill E. Parker, Floresville, TX (US); Johnathan L. Kiel, Universal City, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 278 days.

(21) Appl. No.: 10/339,259

(22) Filed: Jan. 6, 2003

Related U.S. Application Data

(60) Provisional application No. 60/351,064, filed on Jan. 24, 2002.

(51) Int. Cl.[7] ............................ C12Q 1/68; C07H 21/04
(52) U.S. Cl. ......................................... 435/6; 536/24.32
(58) Field of Search ............................ 435/6; 536/24.32

(56) References Cited

U.S. PATENT DOCUMENTS

| 5,156,971 A | 10/1992 | Kiel et al. |
| 6,087,104 A | 7/2000 | Yamada et al. |
| 6,448,016 B1 | 9/2002 | Rastogi et al. |

OTHER PUBLICATIONS

Johnathan L. Kiel, Jill E. Parker, John L. Alls, John Kalns, Eric A. Holwitt, Lucille J.V. Stribling, Pedro J. Morales, John G. Bruno, Rapid Recovery and Identification of Anthrax Bacteria from the Environment, Annals of the New York Academy of Sciences, vol. 916, pp 240–252, Dec. 2000.

P. Keim, A.M. Klevytska, L.B. Price, J.M. Schupp, G. Zinser, K.L. Smith, M.E. Hugh–Jones, R. Okinaka, K.K. Hill, P.J. Jackson, Molecular diversity in *Bacillus anthracis*, Journal of Applied Microbiology 1999, 87, 215–217 (publ 1999).

Erlendur Helgason, Ole Andreas Økstad, Dominique A. Caugnant, Henning A. Johansen, Agnes fouet, Michele Mock, Ida Hegna, Anne–Brie Kolstø, Bacillus anthracis, *Bacillus cereus*, and *Bacillus thuringiensis*—One Species of the Basis of Genetic Evidence, Applied and Environmental Microbiology, Jun. 2000, p 2627–2630 (publ Jun. 2000).

*Primary Examiner*—Mark Navarro
(74) *Attorney, Agent, or Firm*—AFMCLO/JAZ; Charles E. Bricker

(57) ABSTRACT

A PCR-based method for the identification of *Bacillus anthracis* is described. The method utilizes novel primer sets; designated 2Xlg3F (SEQ ID NO 3), 2Xlg3R (SEQ ID NO 4), 2Xlg3F$_2$ (SEQ ID NO 5), 2Xlg3R$_2$ (SEQ ID NO 6), 4XH1a$_2$F (SEQ ID NO 7), and 4XH1a$_2$R (SEQ ID NO 8).

10 Claims, No Drawings

DNA PROBES FOR SPECIFIC GENES OF ANTHRAX

CROSS REFERENCE TO RELATED APPLICATION

This application claims priority of the filing date of Provisional Application Ser. No. 60/351,064, filed Jan. 24, 2002, the entire contents of which are incorporated by reference.

RIGHTS OF THE GOVERNMENT

The invention described herein may be manufactured and used by or for the Government of the United States for all governmental purposes without the payment of any royalty.

BACKGROUND OF THE INVENTION

The present invention relates to the detection of *Bacillus anthracis*.

Anthrax, primarily a disease of herbivorous animals but of rare occurrence in humans, is caused by *Bacillus anthracis*. Cutaneous anthrax is acquired via injured skin or membranes, entry sites where the spore germinate into vegetative cells. Proliferation of vegetative cells results in gelatinous edema. Alternatively, inhalation of the spores results in high fever and chest pain. Both types can be fatal unless the invasive aspect of the infection can be intercepted. *Bacillus anthracis* is a biological warfare (BW) agent. Ten grams of anthrax spore can kill as many people as a ton of the chemical warfare agent, sarin. Due to the highly lethal nature of anthrax and BW agents in general, there is great need for the development of sensitive and rapid BW agent detection. Current detection technology for biological warfare agents have traditionally relied on time-consuming laboratory analysis or onset of illness among people exposed to the BW agent.

In theory, the use of specific antibodies or distinguishing DNA probes are the two approaches to modernizing detection technology in this field. However, antibody-based detection of threat agents suffers from drawbacks. For example, interference from other environmental contaminants precludes detection, or detection limits of current levels fail to meet the detection thresholds set by governmental testing protocols. Alternatively, the threat agent, such as with anthrax spore, may be poorly immunogenic.

Since a sample suspected of containing a BW agent like *B.anthracis* could contain such a small yet lethal amount of spores, and an overwhelming amount of other interfering materials, the ability to amplify the agent's genomic material affords a choice of target sites for developing signature probes for specific detection of that agent. Development of highly discriminating techniques are crucial to achieving the stated goals of rapid and sensitive BW detection.

Current PCR-based detection methods of *B.anthracis* rely on the use of primers amplifying tripartite exotoxin genes and/or the polyglutamic capsule genes. Both sets of genes comprise virulence factors and are located on the two indigenous plasmids of anthrax bacteria, pXO1 (174 kbp; toxin) and pXO2 (95 kbp; capsule). Under normal conditions, the two plasmids in *B.anthracis* do not move across the related bacilli of the "*B. cereus* group", which is comprised of *B. anthracis, B. cereus, B. thuringiensis* and *B. mycoides* (although *B. mycoides* does not produce toxin and therefore may be grouped differently from the other three members). However, under certain conditions, these plasmids are known to be transferred from *B. anthracis* to *B. cereus* and *B. thuringiensis*. Yet *B. cereus* and *B. thuringiensis* containing one or both of these plasmids do not cause anthrax. Therefore, detection of anthrax based solely on virulence factors can give rise to a false-positive determination.

Two chromosomal DNA fragment sequences from *B. anthracis* have been previously identified and used in identifying the presence of *B. anthracis* bacteria. One, designated Ba813, is a 277 bp long DNA fragment and the other, vrrA, is a region of sequence variability containing variable repeats (caa tat caa caa).

Additionally, Yamada et al (U.S. Pat. No. 6,087,104) identified unique regions of the DNA gyrase sub-unit B (gyrB) gene for each of the closely related bacteria of the *B. cereus* group, and designed oligonucleotide primers corresponding to those unique regions for amplification-based detection methods. However, amplification of DNA segments unique to each of the *B. cereus* group members occurred only when the correct target strain DNA by itself was present in the PCR protocol.

Since the development of more rapid and more sensitive BW detection methodologies is of such importance to the military as well as public health sectors of the U.S. government, there is great need to continue the process of identifying, cloning, and sequencing of polymorphic DNA markers from chromosomal DNA of threat agents.

Accordingly, it is an object of the present invention to provide a method for the detection of *B. anthracis*.

It is another object of the present invention to provide primer pairs for the PCR amplification-based detection of *B. anthracis*.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with one embodiment of the present invention there are provided primer pairs (SEQ ID NOS: 3–8) for the PCR amplification-based detection of *B. anthracis*.

In another embodiment of the invention these primer pairs are used in diagnostic assays to accurately analyze samples for environmental contamination by *B. anthracis* spores and for the early diagnosis of anthrax.

DETAILED DESCRIPTION OF THE INVENTION

In the present invention specific primers are used under low-stringency annealing temperatures with genomic DNA from a given BW agent such as *B. anthracis* and its close relatives in PCR protocols. The number and size of amplified fragments derived from genomic DNA of a desired BW agent under these conditions depend on the existing number of priming sites and the distance between the priming sites in opposite direction on the two strands of DNA. In practice, the number and size of amplified fragments depend on the ability of a single primer to anneal to complementary sites on the two strands in opposite directions (5'→3' and 3'→5') within about 2500 bp of each other. Identification, cloning, and obtaining of sequence information from polymorphic DNA markers located on the chromosomal DNA enables the formation of a library of agent-specific signature sequences, also referred to as a DAF pattern (DNA Amplification Fingerprinting pattern). As between the closely-related members of a group such as B. cereus RAPD (random amplified polymorphic DNA) produces a common sub-set of amplified DNA fragments since the genomes are largely similar. However, there will be a further sub-set of amplified fragments unique to each individual member on account of inherent DNA polymorphisms.

A general outline and brief description of the methods utilized in the present invention in order to elucidate DNA markers from the chromosomal DNA of B. anthracis follows. A more detailed description is provided in the "Examples" section.

DNA from B. anthracis strain Sterne was prepared following standard procedures known to one of ordinary skill for isolation of genomic DNA. The DNA was digested with BamH1 endonuclease, and the BamH1 fragments were cloned into a BamH1 Predigested ZAP expression vector (Stratagene, Inc.) and cloned in E. coli. XL1-Blue MRF'.

The cloned cells were amplified following standard procedures. Aliquots of the amplified library were plated on 3AT plates (2X, 4X, 6X, 8X and 2XJ with reference to 3AT, nitrate and luminol concentration) as disclosed in U.S. Pat. No. 5,156,971, Kiel et al, 1992.

DNA from the amplified, cloned cells was prepared, again following standard procedures. The BamH1 endonuclease digested DNA was electrophoresed in a 0.8 agarose gel using TAE (0.04M Tris acetate, 0.001M EDTA) buffer. Fragments were sized by comparing with standards Hind III digested lambda phage (λ) and Hae III digested PhiX174 (φX174).

The cloned B.anthracis DNA fragments were subjected to polymerase chain reaction (PCR) to purify inserts, using Gene Choice TAQ polymerase (PGC Scientific), and T3 and T7 primers (Gibco). The size of the PCR products were compared with insert sizes (due to the position of the BamH1 site in the Multiple Cloning Site PCR products were approx. 150 bp greater in size than BamH1 inserts) and precipitated. Precipitates were dissolved in DNA buffer and used for dideoxy sequencing using Stratagene Cyclist sequencing kit and $^{33}$P dATP. Primers used were T3 or T7. Products were run on 6% polyacrylamide denaturing gels with Tris/borate (0.089 M Tris HCl, 0.027M EDTA, 0.089 M boric acid) buffer pH8.3 at constant 44W. Resulting sequence data was confirmed against The Institute for Genomic Research (TIGR) database for the Ames strain of anthrax bacillus.

Digests of genomic DNA prepared as described above of Pseudomonas aeruginosa, Pseudomonas stutzeri, Bacillus licheniformis, B. thuringiensis, B. cereus, B. globigii v. niger, and B. anthracis (Sterne) with BamH1 were made. An aliquot from each bacterial digest was subjected to electrophoresis in a 1% agarose gel in TAE buffer for Southern blotting.

Probes were made from the sequenced PCR inserts from the library using the precipitated, dissolved PCR product and a Random Primer labeling kit (Gibco). Radionucleotide $^{32}$P dCTP was used to label the DNA.

Samples were collected and read on a Bioscan/QC.4000XER counter. Peak tubes were pooled for use as the probe.

Sequences from probes giving unique patterns with B.anthracis DNA compared with the other bacterial species were subjected to DNASIS (Hitachi) primer search programme and primers were made for these fragments by Sigma-Genosys, 1442 Lake Front Circle, The Woodlands, Tex. 77380.

Primers were tested against B.anthracis Sterne, B.anthracis Alls/Gifford strain, a B. anthracis phage resistant strain, B. anthracis Vollum strain Bacillus licheniformis, B. thuringiensis, B. cereus and B. globigii v. niger by PCR.

Two B.anthracis sequences were identified (SEQ ID NO: 1–2) as being unique in their ability to distinguish between anthrax DNA and the DNA of the remaining members of the B. cereus family. In these sequences, the BamH1 sites are shown in bold type and the primer sites are italisized and double-underlined. Based on results of the Southern blots, primer sets were made to SEQ ID NO: 1 and SEQ ID NO: 2. An additional set of primers was made to SEQ ID NO: 1 outside of the BamH1 sites. The primer sets are designated SEQ ID NO: 3–8. All sequences were 30-mers except SEQ ID NO: 5, a 20-mer. SEQ ID NO: 3 and 4 amplify a fragment of SEQ ID NO: 1 within the BamH1 sites providing a sequence of 1041 bp; SEQ ID NO: 5 and 6 amplify a fragment of SEQ ID NO: 1 outside the BamH1 sites providing a sequence of 1342 bp; and SEQ ID NO: 7 and 8 amplify a fragment of SEQ ID NO: 2 providing a sequence of 2302 bp.

Primers according to the invention may optionally have a detectable label or tag conjugated thereto. Suitable labels or tags are well-known to those working in the field, and, for example, may be chosen to provide a radioactive, calorimetric, fluorometric or luminescent signal depending on the particular application. Incorporation of an appropriate visualization label into custom-synthesized primers and probes follows routine protocol of the DNA synthesizer employed. It is within the preferred scope of the invention, for example, that the primers herein described be synthesized to incorporate a fluorescent tag so that detection of anthrax organism can be carried out on a Taq-man® platform or other suitable diagnostic medium.

These novel primers of this invention are useful in PCR assays These primers are used for amplification of the target DNA contained in the sample.

The amplification-based method for detection of B. anthracis in a sample comprises (a) preparing DNA from a sample, (b) subjecting the DNA to PCR using at least one of the primer sets described previously, preferably SEQ ID NO: 3 and 4 to amplify a fragment of SEQ ID NO: 1 and SEQ ID NO: 7 and 8 amplify a fragment of SEQ ID NO: 2, or SEQ ID NO: 5 and 6 to amplify a fragment of SEQ ID NO: 1 and SEQ ID NO: 7 and 8 amplify a fragment of SEQ ID NO: 2, and (c) detecting the amplificates. The detection step following the amplification step may be carried out by any means as far as it is effective for detecting DNA, such as agarose gel electrophoresis followed by staining with ethidium bromide.

The primer set SEQ ID NO:7 and SEQ ID NO:8 amplifies the sequence of 2302 bp in Bacillus anthracis. The presence of the amplified fragment could not be confirmed in Bacillus cereus, Pseudomonas aeruginosa, Bacillus licheniformis, Pseudomonas stutzeri, Bacillus globigii v. niger, or Bacillus thurigenisis, which shows biochemical properties very similar to those of Bacillus anthracis.

The primer sets SEQ ID NO:3/4 and SEQ ID NO:5/6 amplify the sequences of 1041 bp and 1342 bp, respectively, in Bacillus anthracis. The presence of these amplified fragments could not be confirmed in Pseudomonas aeruginosa, Bacillus licheniformis, Pseudomonas stutzeri, Bacillis globigii v. niger, or Bacillus cereus. These findings demonstrate that the primers of this invention are specific to Bacillus anthracis and thus can be used for its detection.

The following examples illustrate the invention:

Example 1

Genomic DNA Preparation

Chromosomal DNA was prepared from Sterne strain *Bacillus anthracis*. A single colony of *B. anthracis* was isolated from a tryptic soy (TSB) agar plate inoculated with a drop of Thraxol-2 Anthrax Spore Vaccine (Mobay Corp., Shawnee, Kans.). The plate was allowed to grow overnight at 37° C. Next day a single colony was removed and used to inoculate 2 ml of TSB. This was incubated overnight at 37° C. and next day was used to inoculate 100 ml of TSB, which was incubated for 2 days at 37° C.

The cells were harvested by centrifugation at 8,000 rpm in a Sorvall RC 5B and SS34 rotor at 4° C. Care was taken in removing the supernatant from the flocculent pellet. The pellet was resuspended in 10 ml 0.32M sucrose, 10 mM Tris HCl pH 7.5, 5 mM $MgCl_2$ solution, and left on ice for 15 min. The suspension was centrifuged as described above. After centrifugation the supernatant was poured off. Resuspension of the pellet was accomplished in 4.5 ml 0.075M NaCl, 0.024M EDTA solution, 0.5 ml 5% SDS and 100 $\mu$l Proteinase K (10 mg/ml). The suspension was mixed and left overnight at 37° C. After incubation, 2.5 ml of phenol equilibrated with DNA buffer (10 mM Tris HCl pH 8.0, 1 mM EDTA) was added and the mixture was shaken vigorously, centrifuged briefly, and 2.5 ml chloroform/isoamyl alcohol (24:1 v/v) was added. The mixture was shaken vigorously and centrifuged at 2,500 rpm for 5 min at room temperature. The upper aqueous layer was removed to a clean tube and reextracted with 5.0 ml chloroform/IAA. After shaking, the mixture was centrifuged at 2,500 rpm for 2 min and the top layer remove to a clean tube. To precipitate the DNA 2.2 vol of ice-cold ethanol and $\frac{1}{10}^{th}$ vol of 3M sodium acetate were added and the solution mixed by inversion. The resulting spooled DNA was removed with a sterile tip and dissolved in DNA buffer. The concentration was calculated from reading 1 $\mu$l at $^{260}/_{280}$ nm with a Spectronic Genesys 5 spectrophotometer.

Example 2

Library Preparation

An expression library was generated from 25 $\mu$g *B.anthracis* DNA digested with BamH1 endonuclease. The BamH1 fragments were cloned into a BamH1 Predigested ZAP expression vector (Stratagene, Inc.) and cloned in *E. coli*. XL1-Blue MRF'. The library was titered by plating dilutions ($10^{-3}$–$10^{-15}$) on 100 mm NZY plates. To amplify the library thirty-seven aliquots of 18 $\mu$l of a $2 \times 10^{-6}$ dilution were plated on 150 mm NZY plates by mixing with 600 $\mu$l XL1-Blue MRF' cells (OD 0.5) in LB broth and incubating at 37° C. for 15 min. Molten NZY top agar at 47° C. was added before pouring onto the NZY plates. The plates were incubated for 8 hours at 37° C. To each plate 10 ml SM solution was added and the plates were incubated with gentle shaking at 4° C. overnight. The solution was removed next day and the plates washed with a further 2 ml of SM solution. All supernatants were pooled and chloroform added to give a 5%(v/v) final concentration. The supernatants were mixed well, incubated at room temperature for 15 min and spun at 1,000 g for 10 min to remove debris. Chloroform was added to a final concentration of 0.3 (v/v), and the supernatants stored at 4° C. Three 500 $\mu$l aliquots were removed, DMSO added to a final concentration of 7% (v/v) and the aliquots stored at −80° C. Aliquots of the amplified library each calculated to give 50,000 pfu were mixed with 200 $\mu$l *E. coli* XL1-Blue MRF' cells grown in LB broth supplemented with 10 mM $MgSO_4$ and 0.2% maltose and diluted to 0.5 OD. After 15 min incubation at 37° C. 3.0 ml NZY top agar was added and cells plated on 3AT plates (2X, 4X, 6X, 8X and 2XJ with reference to 3AT, nitrate and luminol concentration) were used as in Kiel et al, U.S. Pat. No. 5,156,971, 1992, but all plates contained 55 g/l TSA, a concentration 1.375 greater than recommended by the manufacturer (Difco). A few plates were plated with IPTG, a substrate for $\beta$-galactosidase, with the intent of inducing and selecting for genes of certain enzymic pathways during growth. A second experiment was performed 6 months later (no ITPG was used) and resulting plaques were processed as those from the first plating.

Plaques were cored from the plate with a sterile toothpick and soaked overnight in 500 $\mu$l SM solution. Chloroform, 5% (v/v), was added to preserve the resulting virus particle suspension. Samples were stored at 4° C. for up to one year. The virus particles were used to infect host cells *E. coli* XL1-Blue MRF'. The XL1-Blue MRF' cells were grown in NZY broth supplemented with 10 mM $MgSO_4$ and 0.2% maltose. Cells were resuspended in 10 mM $MgSO_4$ to O.D. 1.0. An aliquot of the cells (200 $\mu$l), Ex-Assist helper phage (1 $\mu$l $1 \times 10^7$ pfu) and a 1 $\mu$l aliquot of bacteriophage from the library were incubated for 15 min at 37° C. After incubation 3.0 ml of NZY broth was added and the samples shaken gently overnight at 37° C. The tubes were removed, heated to 68° C. for 20 min, spun and the supernatant remove to a clean tube. The supernatant contained phagemid with *B.anthracis* insert. *E. coli* XLOLR cells, grown in LB broth to OD 1.0 were resuspended to OD 1.0 in 10 mM $MgSO_4$. An aliquot of the cells (200 $\mu$l) and 10 $\mu$l aliquot of the phagemid suspension were incubated at 37° C. for 15 min. After incubation, cells were diluted with 0.3 ml NZY broth and incubated further for 45 min at 37° C. A 50 $\mu$l aliquot was plated on LB-Kanamycin (50 $\mu$g/$\mu$l) plates.

Example 3

Mini-Preps for DNA

Individual colonies were grown up in 2.0 ml LB-kanamycin (50 $\mu$g/$\mu$l) liquid cultures overnight at 37° C. with shaking. Three colonies were picked from each plate and DNA mini preps performed. Cells were centrifuged at 14,000 rpm for 2 min at 4° C. and the pellet suspended in 100 $\mu$l Solution I (50 mM glucose, 10 mM EDTA pH 8.0, 25 mM Tris HCl pH 8.0), and 200 $\mu$l of Solution II containing 0.2N NaOH and 0.5% SDS was added. Tubes were inverted to mix and 150 $\mu$l Solution III (5M potassium acetate pH 5.5) added. The tubes were vortexed inverted and left on ice for 10 min before centrifuging at 14,000 rpm for 5 min at 4° C. The supernatant was removed to a clean tube, 10 $\mu$l RNAase A (10 mg/ml in water) was added, and the mixture incubated for 30 min at 37° C. After incubation, the solution was phenol/chloroform extracted using 400 $\mu$l of equilibrated phenol and 400 $\mu$l chloroform. After shaking vigorously, the tubes were spun at 14,000 rpm at RT for 5 min. The supernatant was removed to a clean tube and DNA was precipitated using 2.2 vol ice-cold ethanol and $\frac{1}{10}^{th}$ vol 3 M sodium acetate. The mixture was mixed well, left on ice for 10 min and centrifuged at 14,000 rpm for 5 min at 4° C. The pellet was rinsed with 200 $\mu$l of 75% ice cold ethanol and centrifuged at 14,000 rpm for 2 min at 4° C. The pellet was air dried and dissolved in 30 $\mu$l DNA buffer (10 mM Tris HCl pH 8.0, 1 mM EDTA).

Example 4

Characterization of Insert

Phagemid DNA was digested with BamH1 restriction endonuclease in a reaction mixture containing $1/10^{th}$ final volume DTT(1 mM), BSA (1 µg/ml) 10× buffer 3 (Gibco), 5 µl DNA solution and 5–10 U BamH1 restriction endonuclease. Samples were incubated at 37° C. for 1 hr. After incubation samples were electrophoresed in a 0.8 agarose gel using TAE (0.04M Tris acetate, 0.001M EDTA) buffer. Fragments were sized by comparing with standards Hind III digested lambda phage (λ) and Hae III digested PhiX174 (φX174).

Cloned B.anthracis DNA fragments were subjected to polymerase chain reaction (PCR) to purify inserts. A 1 to 10 dilution of the mini prep DNA was made. PCR reaction mix contained 10×PCR buffer (PGC Scientific), 2.6% DMSO, 2 mM dNTPs, 2U Gene Choice TAQ polymerase (PGC Scientific), 200 nM each T3 and T7 primers (Gibco) in a 50 $\mu$l reaction volume. PCR conditions using a Perkin Elmer 9600 were 96° C. for 2 min, then 94° C. for 1 min, 50° C. for 1 min, 72° C. for 1 min for 35 cycles, followed by 72° C. for 5 min. The size of the PCR products were compared with insert sizes (due to the position of the BamH1 site in the Multiple Cloning Site (MCS) PCR products were approx. 150 bp greater in size than BamH1 inserts) and precipitated using an equal volume of 5M ammonium acetate pH 5.5 and 2 volumes of isopropanol. Precipitates were dissolved in 10 $\mu$l DNA buffer and 1 $\mu$l used for dideoxy sequencing using Stratagene Cyclist sequencing kit and $^{33}$P dATP. Primers used were T3 or T7. PCR conditions for sequencing using a Perkin Elmer 9600 were 95° C. for 1 min, then 95° C. for 30 sec, 60° C. for 30 sec, 72° C. for 30 sec for 30 cycles. Products were run on 6% polyacrylamide denaturing gels with Tris/borate (0.089 M Tris HCl, 0.027M EDTA, 0.089 M boric acid) buffer pH8.3 at constant 44W. Dried gels were exposed to X-ray film. Resulting sequence data was confirmed against The Institute for Genomic Research (TIGR) database for the Ames strain of anthrax *bacillus.*

Digests of 60 $\mu$g of genomic DNA prepared as described above of *Pseudomonas aeruginosa, Pseudomonas stutzeri, Bacillus licheniformis, B. thuringiensis, B. cereus, B. globigii* v. niger, and *B. anthracis* (Sterne) with BamH1 in 500 $\mu$l were made. An aliquot from each bacterial digest containing 10 $\mu$g of digested DNA was subjected to electrophoresis in a 1% agarose gel in TAE buffer for Southern blotting. After separating the DNA, the gel was photographed with a ruler and the gel was soaked with gentle shaking in 2 washes of 20 min each in 0.5M NaOH1.5M NaCl. The gel was then neutralized in 0.5M Tris HCl pH7.5/1.5M NaCl for 2 washes 20 min each. The gel was inverted and Nitroplus 2000 (Micro Separations Inc.) was used to blot the gel in 20×SSC (3.0 M NaCl, 0.3M sodium citrate) overnight. The membrane was removed, air-dried and baked for 2 hr under vacuum at 80° C. This was repeated for as many probes as were to be tested.

Probes were made from the sequenced PCR inserts from the library using 1 $\mu$l of the precipitated, dissolved PCR product and a Random Primer labeling kit (Gibco). Radionucleotide $^{32}$P dCTP was used to label the DNA. Unincorporated label was removed using a G-50-filled pasteur pipette column in SET (50 mM Tris HCl pH 7.5, 1 mM EDTA, 100 mM NaCl). Elution was performed in SET with 0.1% SDS added. Samples of 100 $\mu$l were collected and read on a Bioscan/QC.4000XER counter. Peak tubes were pooled for use as the probe.

The Southern blot was prehybridized for 2 hr at 42° C. using 50% Formamide, 6×SSPE (20×SSPE is 20 mM EDTA, 0.16M NaOH, 0.2 M $NaH_2PO_4$, 3.6 M NaCl), Denhardts (0.02% final BSA, Ficoll, polyvinylpyrrolidone) 5% Dextran sulfate and heat denatured Salmon sperm DNA (1 mg/ml). Hybridization was performed overnight under the same conditions and with heat denatured probe added to the hybridization solution. The filter were washed in 2×500 ml washes of 2×SSC/0.1% SDS for 20 min, 2×500 ml washes of 0.2×SSC/0.1% SDS and 2×500 ml washes of 0.1×SSC/0.1% SDS. The filter was air dried and exposed to x-ray film (PGC Scientific).

Probes giving unique patterns with *B.anthracis* DNA compared with the other bacterial species were subjected to DNASIS (Hitachi) primer search programme and primers (Sigma Genosys) were made for these fragments. Primers were tested against *B. anthracis* Sterne, *B.anthracis* Alls/Gifford strain, a *B. anthracis* phage resistant strain, *B. anthracis* Vollum strain *Bacillus licheniformis, B. thuringiensis, B. cereus* and *B. globigii* v. niger by PCR using the following program: 96° C. for 2 min, then 94° C. for 1 min, 60° C. for 1 min, 72° C. for 1 min for 35 cycles, followed by 72° C. for 5 min. Annealing temperatures from 45° C. to 65° C. using 5° C. increments were tested to ensure that there was no product formation in other species at other temperatures with the primer sets.

Having thus described exemplary embodiments of the present invention, it should be noted by those skilled in the art that the disclosures herein are exemplary only and that alternatives, adaptations and modifications may be made within the scope of the present invention.

We claim:

1. A pair of forward and reverse primers for use in the amplification-based detection of *Bacillus anthracis*, said primer pair consisting of SEQ ID NO:3 and SEQ ID NO:4 wherein said primer pair specifically amplifies *Bacillus anthracis* DNA and do not amplify DNA from related strains of *Bacillus cereus* or *Bacillus thuringienis*.

2. The primer pair of claim 1, further including a detectable label.

3. A pair of forward and reverse primers for use in the amplification-based detection of *Bacillus anthracis*, said primer pair consisting of SEQ ID NO:5 and SEQ ID NO:6 wherein said primer pair specifically amplifies *Bacillus anthracis* DNA and do not amplify DNA from related strains of *Bacillus cereus* or *Bacillus thuringienis*.

4. The primer pair of claim 3, further including a detectable label.

5. A pair of forward and reverse primers for use in the amplification-based detection of *Bacillus anthracis*, said primer pair consisting of SEQ ID NO:7 and SEQ ID NO:8 wherein said primer pair specifically amplifies *Bacillus anthracis* DNA and do not amplify DNA from related strains of *Bacillus cereus* or *Bacillus thuringienis*.

6. The primer pair of claim 5, further including a detectable label.

7. A method for the detection of *Bacillus anthracis* in a sample comprising the steps of (a) preparing DNA from a sample, (b) subjecting the DNA to PCR using the primer set described as SEQ ID NO: 3 and 4 to amplify a fragment of SEQ ID NO: 1, and SEQ ID NO: 7 and 8 to amplify a fragment of SEQ ID NO: 2, and (c) detecting the amplificates.

8. The method of claim 7 wherein said detection step is carried out by gel electrophoresis followed by staining with ethidium bromide.

9. A method for the detection of *Bacillus anthracis* in a sample comprising the steps of (a) preparing DNA from a sample, (b) subjecting the DNA to PCR using the primer set described as SEQ ID NO: 5 and 6 to amplify a fragment of SEQ ID NO: 1, and SEQ ID NO: 7 and 8 to amplify a fragment of SEQ ID NO: 2, and (c) detecting the amplificates.

10. The method of claim 9 wherein said detection step is carried out by gel electrophoresis followed by staining with ethidium bromide.

* * * * *

SEQUENCE LISTING

```
<160> NUMBER OF SEQ ID NOS: 8

<210> SEQ ID NO 1
<211> LENGTH: 2060
<212> TYPE: DNA
<213> ORGANISM: Bacillus anthracis

<400> SEQUENCE: 1
atcgtaaaac acaagatatt gttgagaaaa aagcagaaat tgttacaact taccatgaag     60
gcatggagcc tgataaaaaa ataaagaaga agatggagaa atatcaagca aaaatcgcac    120
```

```
ctcttgttaa tgaagttgta ggtaagtcta ttgctccgct agatcgcaaa ctaaatacgg      180
ctggtgaatc tactcttgga aatttagttg ctgatgccca gcgtgcaaca atgcaatctc      240
aaattgcact tatgaatcct ggtggtattc gtaatgactt agatgctggt gatattacat      300
ggggagagat atatggtatt caaccattcg gaaatcaatt aataaaagta aatttaacgg      360
gtcaagatat tcgtgatatt ttaaatcaac aatggcaaaa agacataaca agaatgcttc      420
aaatttcagg gatccaatac acttgggatg caaacaaacc taatggagaa aaagtaacaa      480
gtattcgcct aacaaatgga gaagaaatta ttccttctaa aacttacagc gtcgttgcga      540
acgcatttct agcttcaggt ggagatggat ttgtatcctt aaaaacggt aaagatgctg       600 aaacaggacc aactgatttt gaagcattag tagattacat aaaaaaatca aaagaaccaa      660
ttcagtctat tattgatgga agaattcaaa aaataaatta ggttttatt aatcacaaaa        720 aaatagatta cctatacttt ttagtgtaca ggtaatctat tttttatggg tttgaaataa      780
cgtcttactg tgaccaatta atagtaacgg taaatttggc ccctatggaa cattaaaatc      840
agatgatcca aacagttaaa actacatctt tggacaagtt aaaaagatca aattttatt       900 gatttacgta aggcaaacgg agtgacaaaa acttggttaa gcaacaaca tctaattttc       960 gctgagataa ctaccgaagt gcctgatata ccaaaaactg ttgatatatc attaggtaaa     1020
tcatttgata tacttgttca aattcaaaaa gtgagtccat ctcaattttt tgctgtttaa     1080
cagtttgtat tacgaagcta ttaacaatgg aaaagggaga atgtaactag ttatgcagat     1140
gaatcttggc acatccgcta tgtaggagca gcgtttgtaa aattaaaaat tgaaatagtt     1200
gtaactatag tcttagataa tacgaaagac atagtggggt aggttaagtt gattttgctt     1260
taatctgtaa taacagttat aaattaaggt taattatctt atgaaataag aaaaagcatt     1320
ataagttata atgtttactt gtttttttgt tttacttgtt cttttaattc atcaagggtc     1380
ttaccgctaa tattgtcagt aatagtttca tgtatttcat tttttaatac aattgttttt     1440
cctgcaagtt gtgctttgga agacatttta ctttcattaa tagtttctat gtttgtctga     1500
aggtctgctt tgttattttc atcaaaggta attgcgaatg gttcaattgc tccgtagtag     1560
ttaccaaata attgatcctt cttcaaaaac atcatatatt ttttattaat cataggttcg     1620
atatataaag gatccttatt ttgcacctct ttagtagtta tcttagtagc ctttttgta      1680 actgtgccat ctggtgcaat aactgcatta gaatcttcaa gttttacagt ttcagcgaaa     1740
cgatgattga tttttatttg tttattttca ttcacacctt taattgtttc ggaaatgttg     1800
aaattatata gatgtccttc aacgtaattt tctttgtcct cttccgatgg attacttgga     1860
ttacgtgcca tattccactt agagtcaaga ccttcatatt caccgattac aactagatct     1920
gcttcattaa tcatttgatt taaatcactt gtagcaggga atctttact gagaataaca      1980 gtttcggtat tcttatcttc ttcagcaaca ggggagaagt gactattaaa tgctgaatat     2040
cctcccaaac caattactgt                                                  2060

<210> SEQ ID NO 2
<211> LENGTH: 3980
<212> TYPE: DNA
<213> ORGANISM: Bacillus anthracis

<400> SEQUENCE: 2
gattgcgtga acaatataa tataccggta gaagcaactt tagaaattat cggggggaaag      60 tggaaagtcg tcattttatg tcacttaaca aaggtaaga agcgaacgag tgagttgcaa      120
cgtttaattc ctgaaatttc tgttagaatg ttaacgcaac aattacgtga gttagaagaa      180
```

-continued

```
gatggtgtga ttacacgtaa aatctataac gaaattccac ctcgagtaga atactcctta    240
actgattatg gttggtcttt acaaaatgta ttaaaccaat taactgcatg gggagaacga    300
tgcatagata gaaaaaatag taaagttaaa tgaaatctat atatgtaata ttgaaacacc    360
acctattgat gaggtggtgt ttttttcagta taaaacttta aaaagttact acggtgaaaa    420
gtaaggtgct ataccatatc agcagctgtt ttagctaagg tgaatgttta atctatcatt    480
catcataggt actttaaagt gccttcatca ctttaaagta cgtactatgc ttcatcatat    540
aaccgtttta taatgacact cgtagcaaga agtcattacg gttttaagct atgttcaaaa    600
agacttatta actagaatag ttttttgttc aatttttta gtaggagatg tttatatggt    660
tgaagaactt ttttataaaa aaatacttaa aaatcttttt tcagatccag ttcaaattac    720
actttggaat ggagaaacaa tacaatatgg agaaggggaa cctcaatttc atgtaacatt    780
ccataagccg ctttcaaaaa aagagattgc taaggatcct tctattgcat tggtgaagc    840 atatatgaat ggggaccttg aaatagaggg gaatcttgaa aaagcaattc aatctattta    900
taaaaggcag gatagctttt taggtgatag taagttgcaa tatttcaaaa gtaaatggaa    960
tttctcaaaa caaaaaaata aagacgatat tgctcatcat tatgatattg ggaacgattt   1020
ctataaatta tggcttgatg aaacaatgac atattcttgt gcgtatttcc aaaatgagca   1080 agattctttta acgacagctc agcataataa agtgaatcat attttgaaaa agttgaacct   1140
tcaaaaaggt gatacattat tagatattgg ttgcgggtgg ggtgaactca ttacagctgc   1200
cgctaagcag tacggtgtga aagcgatggg ggtaacgtta agtgaggaac aatatgctaa   1260
ggcttccgag cgaattaaac aagagggact tacggattta gttgaagtat ctttacttga   1320
ttaccgtgat attaagaatc aaaaatttga taaaattgtt agtgtaggta tgattgaaca   1380
tgtaggaaaa gacaacatta cgcaatactt tgaaacagtg aatacactac taaatgatgg   1440
tgggatttct ctacttcatt gtattacttc tccggccaat ggtggtgcta cgaatggttg   1500
gattgaaaaa tatatattcc ctggcggata tgttcctgct gttaacgaat taatcacgaa   1560
catgacaaac gaacaatttt tcattgttga tgtggaaagc ctacgtagac attacgggaa   1620
aacattacaa cattgggctc ggaattttga aaatgtaatg gaggaagttc gcaaaacgaa   1680
agatgagcga ttcattcgta tgtggcgttt atatttaaat gcatgtgcag cttcgttctt   1740
tacaggtaat attgatctac atcaatttgt atttacaaaa ggtattaacg atacaattcc   1800
gatgacacgt tcttatatgt atgaataaga gtgggtaatg aagtagctct ttaactactc   1860
atcgagtgta aataaaatga tggtaggaca taagtctata acttaaagtc gagatcggaa   1920
tcagaaaatg atttccatcc cgactttttt gtatataatt ttaaaaacaa aactatatac   1980
ttttaatgat aaaaatatat aataaatata gaatcgaaaa tttatgagca aggaagttga   2040
agaatatgac attaacaatg ggctttattg gatttggaaa atcagctaac cgctatcatt   2100
taccttatgt aaatacacgt gaaaatataa agtaaaaac aattttttgct cgccaaatta   2160 atgaagaatt agcggctcca tataaggaaa aaggtgttag tttcactact aatttggatg   2220
aattattgaa tgataaagaa attcaagtgg tgacggtctg tacgccagca catacgcatt   2280
acgaattagc gaaaaaagtt atacttgctg gaaaatcagt tattgttgaa aaaccatttt   2340
gcgatacagt agaacatgcg aaagaattgt tagctttagg gtgagaaaaa ggtgtagtag   2400
ttatgcctta tcaaaaccga cgttttgatg gtgattttttt agcggtgaag caagttgtag   2460
aacaaggatt ccttggtgat atcgttgagg ttgaatcaca tatcgattat ttccgtcctg   2520
```

-continued

```
gttcaatcaa tcacgaaggt ccgaaagaag aaggttcatt ttatagttta ggtattcata   2580
cgatggaccg tatgatttca ttgtttggcc gtccagatac ggtgacatac gatattcgta   2640
ataatgaagt ggacggtgcg gttgataact attttgatgt tggtctacat tacggaaatc   2700
agctgaaaat taaactgaaa acgaaccatg ttgtagcaaa ggattatcca cgctttatcg   2760
ttcatggaac aaatggatcg tttattaaat acggtgaaga tcagcaggaa atgatttga    2820 aagcaggtat catgcctgag agtgcaggat ttggtgaaga ttcaccgatg tactatggaa   2880
ttgcgaaata tcgcaatgca aacggtgatt ggattgaaaa acaaattaaa acgccgcttg   2940
gtgattacgg tcgcttctat gatgcagcgt atgaaacaat cgtaaatggt gcaccaaaac   3000
ttgtgaaaga tgaagaagca ataacgaata ttgaaatctt agaaaacgga tttgctgcgc   3060
catcaccttc tgtttacaaa cttgaggctt taaacttaaa tgaatagaag agggaataca   3120
gcataaagga ggtatggaaa tggcaagcgg atccacacaa gtaaaatacc tcggcattta   3180
tcaaaaaatg aaacagcaaa ttttagacgg cgaatataag attaacgaaa aaattccaag   3240
tagccccgtc cttgctgaag aatttgatgt ttctgtcctt actataaaaa agcgctgga   3300 tctgttagtt agagacggct acatcattcg ccggcgcgga agtggaacag tcgttcaaga   3360
ttggcgtcag caggaaaaag cacgaatgat tcaaacttta acaggtacaa agctgtttta   3420
tggcagcgag gtagaaagta aaattattga gtttacgatt gtcggtgccg atgaaattat   3480
tgctgaaaaa ttgggcattt cagtaggaga ttttgtatat aaaatcatcc gcctccgcat   3540
cattcacagt attccaacga ttatggagca tacatggatg ccgatttcgg tcattccagg   3600
tgttgaagtt tctgttttag aggaatcaat ctactcccac attcaaaata aactaggcct   3660
tcaagtggga acatccgttg ttagggtaaa aggaattcgc ccggatgata agaaaaagca   3720
gtttatgaac ttaacaaatc aagatttcct aatgagagtg gaacaggtgg cctacttaac   3780
ggatggacgc acttttgaat actcttacgc cgatcacttg ccggaaacct ttgaattcga   3840
aacagttatt actgcaaaaa gttataaaga ggcataaaaa ataggttgag gcgcgtattg   3900
cctcaaccta ttttttgtct tcaatatagt agaaacagct attattcatc ggctgtaata   3960
agcatggatg tgtgcccggt                                               3980
```

<210> SEQ ID NO 3
<211> LENGTH: 30
<212> TYPE: DNA
<213> ORGANISM: Bacillus anthracis

<400> SEQUENCE: 3
gcgtcgttgc gaacgcattt ctagcttcag                                    30

<210> SEQ ID NO 4
<211> LENGTH: 30
<212> TYPE: DNA
<213> ORGANISM: Bacillus anthracis

<400> SEQUENCE: 4
atttggtaac tactacggag caattgaacc                                    30

<210> SEQ ID NO 5
<211> LENGTH: 20
<212> TYPE: DNA
<213> ORGANISM: Bacillus anthracis

<400> SEQUENCE: 5
aacgggtcaa gatattcgtg                                               20

```
<210> SEQ ID NO 6
<211> LENGTH: 30
<212> TYPE: DNA
<213> ORGANISM: Bacillus anthracis

<400> SEQUENCE: 6
gcaccagatg gcacagttac aaaaaaggct                                    30

<210> SEQ ID NO 7
<211> LENGTH: 30
<212> TYPE: DNA
<213> ORGANISM: Bacillus anthracis

<400> SEQUENCE: 7
gaatggggac cttgaaatag agggaatct                                     30

<210> SEQ ID NO 8
<211> LENGTH: 30
<212> TYPE: DNA
<213> ORGANISM: Bacillus anthracis

<400> SEQUENCE: 8
ggatccgctt gccatttcca tacctccttt                                    30
```